(12) United States Patent
D'Azzo et al.

(10) Patent No.: US 7,232,670 B2
(45) Date of Patent: Jun. 19, 2007

(54) TARGETING PROTEINS TO CELLS EXPRESSING MANNOSE RECEPTORS VIA EXPRESSION IN INSECT CELLS

(75) Inventors: Alessandra D'Azzo, Memphis, TN (US); Erik Jacobus Bonten, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 1129 days.

(21) Appl. No.: 09/966,893

(22) Filed: Sep. 28, 2001

(65) Prior Publication Data

US 2002/0077292 A1    Jun. 20, 2002

(51) Int. Cl.
*C12P 9/00*    (2006.01)
*C12N 9/16*    (2006.01)
*A01N 37/18*    (2006.01)
*A61K 31/70*    (2006.01)
*C07K 1/00*    (2006.01)

(52) U.S. Cl. .................. 435/183; 435/69.1; 435/196; 435/213; 435/220; 514/2; 514/21; 530/350

(58) Field of Classification Search .............. 435/69.1, 435/183, 196, 213, 220; 514/2, 21; 530/350
See application file for complete search history.

(56) References Cited

U.S. PATENT DOCUMENTS

| | | | |
|---|---|---|---|
| 5,179,023 A | 1/1993 | Calhoun et al. |
| 5,658,567 A | 8/1997 | Calhoun et al. |
| 5,762,939 A | 6/1998 | Smith et al. |
| 6,183,987 B1 | 2/2001 | van de Weil et al. |
| 6,225,060 B1 | 5/2001 | Clark et al. |

OTHER PUBLICATIONS

Sharp, J. Secreted Proteins and Uses Therof. WO 00/39150. Jul 6, 2000.*
Aeed, P.A. et al, "Glycosylationof recombinant prorenin in insect cells: the insect cell line Sf9 does not express the mannose 6-phosphate recognition signal", *Biochemistry* 33(29):8793-97 (1994).
Aoki, M. et al, "Improvement of neurological symptoms by enzyme replacement therapy for Gaucher Disease Type IIIb", *Eur. J. Pediatr.*, 160(1): 63-64 (2001).
Berg, T. et al, "Purification and characterization of recombinant human lysosomal alpha-mannosidase", *Mol Genet Metab.*, 73(1):18-29 (2001).
Bijsterbosch, M.K. et al, "Quantitative analysis of the targeting of mannose-terminal glucocerebrosida; Predominant uptake by liver endothelial cells", *Eur. J. Biochem*, 237:344-349 (1996).
Bonten, E J et al, "Lysosomal Protective Protein/Cathepsin A" *Journal of Biological Chemistry* 270(44): 26441-26445 (1995).
Bonten, E J et al; "Catalytic Activation in Insect Cells is Controlled by the Protective Protein/Cathepsin A", *Journal of Biological Chemistry* 275(48): 37657-37663 (2000).

Bonten, E J et al, "Correction of lysosomal PPCA and neuraminidase in mouse deficient macrophages after uptake of recombinant baculovirus-expressed proteins", *Amer. J. Hum. Gen. Suppl.* 69(4):Abst 1759 (2001).
Boose, J.A. et al, "Synthesis of a human lysosomal enzyme, beta-hexosaminidase B, using the baculovirus expression system", *Protein Expr. Purif.* 1(2):111-20 (1990).
Bromme, D. et al, "High level expression and crystallization of recombinant human cathepsin S", *Protein Sci.*, 5(4):789-91 (1996).
Calhoun, D.H. et al, "Fabry disease: Isolation of a cDNA clone encoding human α-galactosidase A", *PNAS* 82:7364-68 (1985).
Chen, Y. et al; "Purification and Characterization of Human α-Galactosidase A Expressed in Insect Cells Using a Baculovirus Vector", *Protein Expression and Purification* 20:228-236 (2000).
Coppola, G et al, "Characterization of glycosylated and catalytically active recombinant human alpha-Galactosidase A using a baculovirus vector", *Gene* 144(2):197-203 (1994).
D'Azzo, A., "Biochemical properties of PPCA and neuraminidase", Presentation at Strategies for Therapy of MPS and Related Diseases and 16th Annual MPS Conference held on Jun. 22, 2001 at UCLA.
Davidson, D.J. et al; "Oligosaccharide Processing in the Expression of Human Plasminogen cDNA by Lepidopteran Insect (*Spodoptera frugiperda*) Cells", *Biochemistry* 29(23): 5584-5590 (1990)
Davidson, D.J. et al; "Asparagine-Linked Oligosaccharide Processing in Lepidopteran Insect Cells. Tempor Dependence of the Naturs of the Oligosaccharides Assembled on Asparagine-289 of Recombinant Human Plasminogen Produced in Baculovirus Vector Infected *Spodoptera frugiperda* (IPBL-SF-21AE) Cells", *Biochemistry* 30(25): 6167-6174 (1991).
Davis, T.R. et al; "Intrinsic Glycosylation Potentials of Insect Cell Cultures and Insect Larvae", *In Vitro Cell. Dev.Biol.* 31:659-663 (1995). .

(Continued)

*Primary Examiner*—Tekchand Saidha
*Assistant Examiner*—Christian L. Fronda
(74) *Attorney, Agent, or Firm*—J. Scott Elmer

(57) ABSTRACT

The present invention is based on the discovery that proteins produced in insect cell cultures are glycosylated in a unique manner that causes them to be selectively imported by cells that express mannose receptors on their membranes, particularly macrophages. Proteins that are selectively imported into cells containing mannose receptors are provided, as well as pharmaceutical compositions containing such proteins and methods for producing such proteins. Application of the present invention to produce proteins useful for treating lysosomal storage disorders is also disclosed. Engineering of cells to express mannose receptors so that they will selectively import proteins produced in insect cells is also taught, as well as a protein targeting system using such cells and proteins. Finally, an improved elution buffer for the purification of proteins produced in insect cells from a Concanavalin A column is provided.

8 Claims, No Drawings

OTHER PUBLICATIONS

Desnick, R.J. "Enzyme replacement and beyond", *J Inherit Metab Dis.* 24(2):251-65 (2001).

Eng, C.M. et al, "A phase 1/2 clinical trial of enzyme replacement in fabry disease: pharmacokinetic, substrate clearance, and safety studies", *Am. J. Hum. Genet.*, 68(3): 711-22 (2001).

Hahn, C.N. et al., "Correction of murine galactosialidosis by bone marrow-derived macrophages overexpressing human protective protein/cathepsin A under control of the colony-stimulating factor-1 receptor promoter", *PNAS* 95:14880-85 (1998).

Hollister, J.R. et al, "Engineering lepidopteran insect for sialoglycoprotein production by genetic transformation with mammalian β1,4-galactosyltransferase and α2,6-sialyltransferase genes", *Glycobiology* 11: 1-9 (2001).

Hsu, T. et al, "Differential *N*-Glycan Patterns of Secreted and Intracellular IgG Produced in *Trichoplusia ni* cells", *Journal of Biological Chemistry* 272(14): 9062-9070 (1997).

Ida, H. et al, "Effects of enzyme replacement therapy in thirteen Japanese pediatric patients with Gaucher Disease", *Eur. J. Pediatr.* 106(1): 21-5 (2001).

Ioannou, Y.A. et al, "Fabry disease: preclinical studies demonstrate the effectiveness of alpha-galactosidase a replacement in enzyme-deficient mice", *Am. J. Hum. Genet.* 68(1): 14-25 (2001).

Jarvis, D.L. et al, "Biochemical Analysis of the N-Glycosylation Pathway in Baculovirus-Infected Lepidopteran Insect Cells", *Virology* 212: 500-511 (1995).

Jarvis, D.L. et al; "Modifying the insect cell N-glycosylation pathway with immediate early baculovirus Expression vectors", *Nature Biotechnology* 14:1288-1292 (1996).

Jarvis, D.L. et al; "Engineering N-glycosylation pathways in the baculovirus-insect cell system", *Current Opinion In Biotechnology* 9: 528-533 (1998).

Jarvis, D.L. et al; "Mutational Analysis of the N-Linked Glycans on *Autographa californica* Nucleopolyhedrovirus gp64", *Journal of Virology* 72(12): 9459-9469 (1998).

Jarvis, D.L. et al. "Novel baculovirus expression vectors that proavide sialylation of recombinant glycoproteins in lepidopteran insect cells", *J. Virol.* 75(13): 6223-27 (2001).

Kakkis, E.D. et al, "Enzyme-replacement therapy in mucopolysaccharidosis I", *N. Engl. J. Med.* 344(3): 182-188 (2001).

Kauli, R. et al, "Delayed Growth in Puberty in Pateints with Gaucher Disease Type 1: Natural History And Effects of Splenectomy and/or Enzyme Replacement Therapy", *Isr. Med. Assoc. J.* 2(2): 158-63 (2000).

Kawar, Z. et al, "Insect cells encode a class II α-Mannosidase with Unique properties", *J. Biol. Chem.* 276(19): 16335-40 (2001).

Lew, D.B. et al, "Mitogenic effect of lysosomal hydrolases on bovine tracheal myocytes in culture", *J. Clin. Invest.*, 99: 1969-1975 (1991).

Lew, D.B. et al, "A mannose receptor mediates mannosyl-rich glycoprotein-induced mitogenesis in bovine airway smooth muscle cells", *J. Clin. Invest.* 94:1855-1863 (1994).

Licari, P.J. et al, "Insect Cell Hosts for Baculovirus Expression Vectors Contain Endogenous Exoglycosidas Activity", *Biotechnol. Prog.* 9:146-152 (1993).

Lin, L. et al, "Production and characterization of recombinant human CLN2 protein for enzyme-replacement therapy in late infantile neuronal ceroid lipofuscinosis", *Biochem J.* 357: 49-55 (2001).

Liu, Z. et al, "TNF-α and IL-1α induce mannose receptors and apoptosis in glomerular mesangial but not endothelial cells", *Am. J. Physiol.* 270: C1595-1601 (1996).

Lutz, D.A. et al, "Natural, high-mannose glycoproteins inhibit ROS binding and ingestion by RPE cell cultures", *Exp. Eye Res.* 61: 487-493 (1995).

Magnusson, S. et al, "Endocytosis of ricin by rat liver cells *in vivo* and *in vitro* is mainly mediated by mannose receptors on sinusoidal endothelial cells", *Biochem J.* 291: 749-755 (1993).

Marchal, I. et al, "Glycoproteins from insect cells: Sialylated or Not?", *Biol. Chem.* 382(2): 151-159 (2001).

Martin, B.M. et al, "Glycosylation and processing of high levels of active human glucocerebrosidase in Invertebrate cells using a baculovirus expression vector", *DNA* 7(2): 99-106 (1988).

Ogonah, O.W. et al; "Isolation and Characterization of an Insect Cell Line Able to Perform Complex N-Linked Glycosylation on Recombinant Proteins" *Biotechnology* 14: 197-202 (1996).

Pastores, G.M. et al, "Enzyme-replacement therapy for Anderson-Fabry disease", *Lancet*, 358(9282): 601-603 (Aug. 25, 2001).

Reis eSousa, C. et al, "Phagocytosis of antigens by langerhans cells in vitro", *J. Exp. Med.* 178: 509-519 (1993).

Roulieux-Bonnin, F. et al, "Transcriptional expression of mannose receptor gene during differentiation of human macrophages", *Biochem. Biophys. Res. Comm.* 217: 106-112 (1995).

Rudenko, G. et al, "Three-dimensional structure of the human protective protein; structure of the precursor Form suggests a complex activation mechanism", *Structure* 3(11): 1249-1259 (1995).

Rudenko, G. et al; "The atomic model of the human protective protein/cathepsin A suggests a Structural basis for galactosialidosis", *PNAS* 95: 621-625 (1998).

Sallusto, F. et al, "Dendritic cells use macropinocytosis and the mannose receptor to concentrate macromolecules in the major histocompatibility complex class II compartments: Downregulation by cytokines and bacterial products", *J. Exp. Med.* 182: 389-400 (1995).

Schiffmann, R. et al, "Enzyme replacement therapy in Fabry Disease: a randomized controlled trial", *JAMA*, 285(21): 2743-2749 (2001).

Seo, N. et al, "Mammalian glycosyltransferase expression allows sialoglycoprotein production by baculovirus-infected insect cells", *Protein Expr. Purif.* 22(2):234-41 (2001).

Shepard, V.L. et al, "Isolation and characeterization of a mannose receptor from human pigment epithelium" *Invest. Ophthamol. Vis. Sci.* 32(6): 1779-1784 (1991).

Sly, W.S. et al, "Active site mutant transgene confers tolerance to human beta—glucuronidase withont affecting the phenotype of MPS VII mice", *PNAS* 98: 2205-10 (Feb. 27, 2001).

Stahl, P.D. et al; "The mannose receptor is a pattern recognition receptor involved in host defense", *Current Opinion in Immunology* 10: 50-55 (1998).

Steed, P.M. et al, "Characterization of recombinant human cathepsin B expressed at high levels in baculovirus", *Protein Science* 7(9): 2033-37 (1998).

Stehle, S.E. et al; "A Soluble Mannose Receptor Immunoadhesin Enhances Phagocytosis of *Pneumocystis Carinii* by Human Polymorphonuyclear Leukocytes In Vitro", *Scandinavian Journal of Immunology* 52: 131-137 (2000).

Taylor, M.E., "Structure and Function of the Macrophage Mannose Receptor", *Results and Problems in Cell Differentiation* 33:105-121 (2001).

Tilkorn, A. et al, "High-level baculoviral expression of lysosomal acid lipase", *Methods Mol. Biol.* 109: 177-85 (1999).

Turner, C.T. et al, "Enzyme replacement therapy in mucopolysaccharidosis I: altered distribution and Targeting of alpha-L-iduronidase in immunized rats", *Mol. Genet. Metab.* 69(4): 277-85 (2000).

Uccini, S. et al, "Kaposi's sarcoma cells express the macrophage-associated antigen mannose receptor and develop in peripheral blood cultures of Kaposi's sarcoma patients", *Am. J. Pathol.* 150(3): 929-938 (1997).

Wagner, R. et al *N-Acetyl*-β-Glucosaminidase Accounts for Differences in Glycosylation of Influenza Virus Hemagglutinin Expressed in Insect Cells from a Baculovirus Vector, *Journal of Virology* 70(6): 4103-4109 (1996).

Wraith,J.E., "Enzyme replacement therapy in mucopolysaccharidosis type I: progress and emerging Difficulties", *J Inherit Metab Dis.* 24(2): 245-50 (2001).

Wu, J. et al, "Expression of catalytically active human multifunctional glycogen-debranching enzyme and Lysosomal acid alpha-glucosidase in insect cells", *Biochem. Mol. Biol. Int.* 39(4): 755-64 (1996).

\* cited by examiner

TARGETING PROTEINS TO CELLS EXPRESSING MANNOSE RECEPTORS VIA EXPRESSION IN INSECT CELLS

GOVERNMENT INTERESTS

This invention was made in part with U.S. Government support under National Institutes of Health grant nos. NIH-DK52025, NIH-GM60950 and NIH-CA21765 and was also supported by funds from the Assisi Foundation and the American Lebanese Syrian Associated Charities (ALSAC). The U.S. Government may have certain rights in this invention.

FIELD OF THE INVENTION

This invention relates to methods for producing proteins in insect cells, methods for targeting proteins to particular cell types, and methods for treating lysosomal storage disorders.

BACKGROUND

Protein Production

Proteins can be recombinantly produced using a vast array of expression systems in a wide variety of cells such as bacteria, yeast, insect cells, and mammalian cells. While the same protein produced in these various systems will generally have the same amino acid sequence, the exact form of the protein and amount produced can differ significantly depending upon which expression system and cell type/organism is used for production.

For many mammalian proteins, expression in bacterial expression systems does not produce functional protein because bacteria and other prokaryotes do not post-translationally modify proteins in the same manner as eukaryotic cells. Such post translational modifications include glycosylation, phosphorylation, and signal peptide cleavage. In order to produce functional versions of these proteins, they may have to be expressed in mammalian cells. However, expression of proteins in mammalian cells can be a time consuming and expensive process.

As an alternative to mammalian cell expression, many proteins may be produced in functional form in insect cells. Production of foreign protein in insect cells is generally considered more cost effective and efficient relative to mammalian cell expression and may be preferred where protein with similar or equivalent biological activity can be produced in insect cells. For example, production of biologically active follicle stimulating hormone and $\alpha$-galactosidase in insect cells has been described. See U.S. Pat. Nos. 6,183,987; 5,658,567; and 5,179,023. Insect cells which are used for expression of foreign proteins, typically via infection with a recombinant baculovirus, accomplish most of the same post-translational modifications as mammalian cells, including phosphorylation, N- and O- linked glycosylation, acylation, disulphide cross-linking, and oligomeric assembly.

However, post-translational modifications in insect cells are not identical to those that occur in mammalian cells, and these differences are not completely understood. See, e.g., Davidson, D. J. et al., *Biochemistry* 29: 5584–5590 (1990); Davidson, D. J. et al., *Biochemistry* 30: 6165–6174 (1991); Jarvis, D. L. et al., *Virology* 212(2): 500–511 (October 1995); Ogonah, O. W. et al., *Nat. Biotechnology* 14: 197–202 (1996); Wagner, R. H. et al., *J. Virol* 70: 4103–4109 (1996); Hsu, T. A. et al., *J. Biol. Chem.* 272(14): 9062–9070 (April. 1997); Hollister, J. et al., *Glycobiology* 11: 1–9 (2001); Seo, N. S. et al., *Protein Expr. Purif.* 22(2):234–41 (2001); Jarvis, D. L. et al., *J. Viro.* 75(13): 6223–6227 (2001); Kawar, Z. et al., *J. Biol. Chem* 276(19): 16335–16340 (2001). These differences and their ill-defined nature are generally considered a disadvantage of producing proteins in insect cells. See, e.g. Jarvis, D. L. et al., *Curr. Opin. Biotechnology* 9(5): 528–533 (October 1998); Marchal, I. et al., *Biol. Chem.* 382(2): 151–159(2001).

Lysosomal Storage Disorders

Lysosomal storage disorders (LSDs) are a group of genetically inherited disorders that are characterized by a deficiency of one or more specific lysosomal enzymes which causes an accumulation of undigested material (macromolecules) inside the lysosome. This accumulation causes lysosomes to enlarge, leading eventually to cell degeneration. This process results in accumulation of macromolecules in various tissues and organs of the body causing these organs to function less efficiently, resulting in progressive deterioration in physical and/or mental state, and eventually death. A list of LSDs and their associated enzyme deficiency is provided in the following table 1.

TABLE 1

Lysosomal Storage Disorders

| Disease Name/Synonyms | Enzyme Deficiency | Supporting Reference |
| --- | --- | --- |
| Pompe Disease<br>Type II Glycogen Storage Disease | Acid $\alpha$-1,4 and 1,6 glucosidase (Acid maltase) | Genbank: X55079 |
| GM1 Gangliodsidosis | $\beta$-Galactosidase | Genbank: M34424<br>OMIM: 230500<br>OMIM: 230650<br>OMIM: 230600 |
| Tay-Sachs Disease<br>GM2 Gangliosidosis | $\beta$-Hexosaminidase A | Genbank: AH003579 |
| GM2 Gangliosidosis: AB Variant | $GM_2$ Activator Protein | Genbank: L01439 |
| Sandhoff Disease<br>GM2 Gangliosidosis | $\beta$-Hexosaminadase A & B | Genbank: AH002718 |
| Fabry Disease<br>Trihexosylceramidosis | $\alpha$-Galactosidase A | Genbank: U78027 |
| Gaucher Disease<br>Glucosylceramide Lipidosis | Glucocerebrosidase<br>$\beta$-glucosidase | Genbank: M19285 |

TABLE 1-continued

Lysosomal Storage Disorders

| Disease Name/Synonyms | Enzyme Deficiency | Supporting Reference |
|---|---|---|
| Krabbe Disease<br>Galactosylceramide Lipidosis<br>Globid-Cell Leukodystrophy | Galactosylcebrosidase<br>β-Galactosidase | Genbank: D25283 |
| Niemann-Pick, Types A and B<br>Sphingomyelin-Cholesterol<br>Lipidosis | Acid Sphingomyelinase | Genbank: M81780 |
| Niemann-Pick, Type C | NPC1<br>Transport of Cholesterol to<br>post-lysosomal destinations | Genbank: AF002020 |
| Niemann-Pick, Type D | NPC1<br>Transport of Cholesterol to<br>post-lysosomal destinations | Genbank: AF002020 |
| Farber Disease<br>Farber Lipogranulomatosis<br>Ceramidase Deficiency | Acid Ceramidase | Genbank: U70063 |
| Wolman Disease | Acid Lipase | Genbank: M74775 |
| Cholesterol Ester Storage<br>Disease | Acid Lipase | Genbank: M74775 |
| Hurler Syndrome<br>Mucopolysaccharidosis I<br>(MPS IH/S) | α-L-Iduronidase | Genbank: M74715 |
| Scheie Syndrome<br>Mucopolysaccharidosis I<br>(MPS 1 S) | α-L-Iduronidase | Genbank: M74715 |
| Hurler-Scheie<br>Mucopolysaccharidosis I<br>(MPS IH/S) | α-L-Iduronidase | Genbank: M74715 |
| Hunter Syndrome<br>Mucopolysaccharidosis II (MPS II) | Iduronate 2-Sulfatase | Genbank: AH000819<br>Genbank: M58342 |
| Sanfilippo A (MPS IIIA) | α-N-Acetylglucosaminidase | Genbank: U43572 |
| Sanfilippo B (MPS IIIB) | α-N-Acetylglucosaminidase | Genbank: U43572 |
| Sanfilippo C (MPS IIIC) | Acetyl-CoA-Glucosaminide<br>Acetyltransferase | OMIM: 252930 |
| Sanfilippo D (MPS IIID) | N-Acetylglucosamine-6-<br>Sulfatase | Genbank: Z12173 |
| Morquio A (MPS IVA) | N-Acetylgalactosamine-6-<br>Sulfate Sulfatase | Genbank: AH006681 |
| Morquio B (MPS IVB) | β-Galactosidase | Genbank: M34424<br>OMIM: 253010 |
| Maroteaux-Lamy (MPS VI) | Arylsulfatase B | Genbank: M32373 |
| Sly Syndrome (MPS VII) | β-Glucuronidase | Genbank: M15182 |
| Metachromatic Leukodystrophy | Arylsulfatase A (cerebroside sulfatase) | Genbank: U62317<br>Genbank: X52151 |
| Multiple Sulfatase Deficiency | Arylsulfatase A, B and C | OMIM: 272200 |
| Sialidosis (Mucolipidosis I) | α-Neuraminidase (glycoprotein neuraminidase) | OMIM: 256550<br>Bonten, E. J. et al., J.<br>Biol. Chem. 275: 37657<br>(2000)<br>Genbank: AF040958 |
| I-Cell Disease<br>Mucolipidosis II (ML-II) | UDP GlcNAc: lysosomal-<br>enzyme N-Acetylglucosamine-<br>1-phosphotransferase | OMIM: 252500 |
| Pseudo-Hurler Polydystrophy<br>Mucolipidosis III (ML-III) | UDP GlcNAc: lysosomal-<br>enzyme N-Acetylglucosamine-<br>1-phosphotransferase | OMIM: 252500 |
| Mucolipidosis IV (ML-IV) | Mucolipin-1 | Genbank: AF287269 |
| α-Mannosidosis | α-Mannosidase | Genbank: AH006687 |
| β-Mannosidosis | β-Mannosidase | Genbank: U60337 |
| Fucosidosis | α-L-Fucosidase | Genbank: M29877 |
| Aspartylglucosaminuria | N-Aspartyl-β-Glucosaminidase | Genbank: X55330 |
| Galactosialidosis (Goldberg Syndrome) | Protective Protein/Cathepsin A (PPCA), neuraminidase, and β-Galactosidase | Genbank: M22960<br>OMIM: 256540<br>Rudenko, G. et al.,<br>Structure, 3, 1249<br>(1995); Rudenko, G. et<br>al., Proc. Natl. Acad.<br>Sci. USA 95: 621<br>(1998); Bonten, E. J. et<br>al., J. Biol. Chem. 270:<br>26441 (1995) |
| Schindler Disease | α-N-Acetyl-Galactosaminidase | Genbank: M62783 |
| Cystinosis | Cystine Transport Protein | Genbank: AJ222967 |
| Salla Disease | Sialin | Genbank: AJ387747 |

TABLE 1-continued

Lysosomal Storage Disorders

| Disease Name/Synonyms | Enzyme Deficiency | Supporting Reference |
| --- | --- | --- |
| Infantile Sialic Acid Storage Disorder | Sialin | Genbank: AJ387747 |
| Batten Disease (Juvenile Neuronal Ceroid Lipofuscinosis | Unknown | Genbank: U32680 |
| Infantile Neuronal Ceroid Lipofuscinosis | Palmitoyl-Protein Thioesterase | Genbank: U44772 |
| Prosaposin | Saposins A, B, C or D | Genbank: J03077 |

A number of LSDs have been treated using enzyme replacement therapy and several clinical trials are ongoing in this area. For example, α-Galactosidase A has been used to treat Fabry disease and glucocerebrosidase has been used to treat Gaucher Disease (sold as Cerezyme® by Genzyme Corp.). Additional examples can be found in the following references:

Pastores G M, Thadhani R., "Enzyme-replacement therapy for Anderson-Fabry disease", Lancet 358(9282): 601–3 (August 2001).

Lin L, Lobel P., "Production and characterization of recombinant human CLN2 protein for enzyme-replacement therapy in late infantile neuronal ceroid lipofuiscinosis", Biochem J. 357(Pt 1):49–55. (July 2001).

Schiffmann R. et al., "Enzyme replacement therapy in Fabry Disease: a randomized controlled trial" JAMA. 285(21):2743–9 (June 2001)

Desnick R J., "Enzyme replacement and beyond" J Inherit Metab Dis. 24(2):251–65 (April 2001).

Wraith, J. E., "Enzyme replacement therapy in mucopolysaccharidosis type I: progress and emerging difficulties" J Inherit Metab Dis. 24(2):245–50 (April 2001).

Berg, T. et al., "Purification and characterization of recombinant human lysosomal alpha-mannosidase" Mol Genet Metab. 73(1):18–29 (May 2001).

Sly, W. S. et al., "Active site mutant transgene confers tolerance to human beta-glucuronidase without affecting the phenotype of MPS VII mice" Proc Natl Acad Sci U S A. 98(5):2205–10 (February 2001).

Aoki, M. et al., "Improvement of neurological symptoms by enzyme replacement therapy for Gaucher disease type IIIb", Eur. J. Pediatr. 160(1):63–4 (January 2001).

Ida, H. et al., "Effects of enzyme replacement therapy in thirteen Japanese paediatric patients with Gaucher disease", Eur. J Pediatr. 160(1):21–5 (January 2001)

Eng, C. M. et al., "A phase ½ clinical trial of enzyme replacement in fabry disease: pharmacokinetic, substrate clearance, and safety studies", Am J Hum Genet. 68(3): 711–22 (March 2001).

Kakkis, E. D. et al., "Enzyme-replacement therapy in mucopolysaccharidosis I", N. Engl. J. Med. 18;344(3):182–8 (January 2001).

Ioannou, Y. A. et al., "Fabry disease: preclinical studies demonstrate the effectiveness of alpha-galactosidase A replacement in enzyme-deficient mice", Am. J. Hum. Genet. 68(1):14–25 (January 2001).

Turner, C. T. et al., "Enzyme replacement therapy in mucopolysaccharidosis I: altered distribution and targeting of alpha-L-iduronidase in immunized rats", Mol. Genet. Metab. 69(4):277–85 (April 2000).

Byers, S. et al., "Delayed growth and puberty in patients with Gaucher disease type 1: natural history and effect of splenectomy and/or enzyme replacement therapy" Isr. Med. Assoc. J. 2(2):158–63 (February 2000).

All of the currently approved treatments and clinical trials in this area as exemplified above utilize enzymes produced in mammalian cells. Some of these enzymes associated with LSDs have also been reported to have been expressed in insect cells in the references cited below, but none of these references report the use of insect-produced proteins in humans.

Chen, Y. et al., "Purification and characterization of human alpha-galactosidase A expressed in insect cells using a baculovirus vector", Protein Expr. Purif. 20(2):228–36 (November 2000).

Tilkorn, A. C. et al., "High-level baculoviral expression of lysosomal acid lipase", Methods Mol Biol. 109:177–85 (1999).

Steed, P. M. et al., "Characterization of recombinant human cathepsin B expressed at high levels in baculovirus", Protein Sci. 7(9):2033–7 (September 1998).

Bromme, D., McGrath, M. E., "High level expression and crystallization of recombinant human cathepsin S", Protein Sci. 5(4):789–91 (April 1996).

Aeed, P. A., Elhammer, A. P., "Glycosylation of recombinant prorenin in insect cells: the insect cell line Sf9 does not express the mannose 6-phosphate recognition signal", Biochemistry 33(29):8793–7 (July 1994).

Coppola, G. et al., "Characterization of glycosylated and catalytically active recombinant human alpha-galactosidase A using a baculovirus vector", Gene 144(2): 197–203 (July 1994).

Boose, J. A. et al., "Synthesis of a human lysosomal enzyme, beta-hexosaminidase B, using the baculovirus expression system", Protein Expr. Purif 1(2): 111–20 (November 1990).

Martin, B. M. et al., "Glycosylation and processing of high levels of active human glucocerebrosidase in invertebrate cells using a baculovirus expression vector", DNA 7(2):99–106 (March 1988).

Wu, J. Y. et al., "Expression of catalytically active human multifunctional glycogen-debranching enzyme and lysosomal acid alpha-glucosidase in insect cells", Biochem. Mol. Biol. Int. 39(4):755–64 (July 1996).

SUMMARY OF THE INVENTION

The present invention is based on the discovery that proteins produced in insect cells by standard baculovirus expression systems are glycosylated in a unique way which makes them susceptible to uptake by macrophages via mannose receptors that are present on macrophage membranes but which are not normally present on the membranes of other cells. Accordingly, the invention provides a method for targeting a protein for uptake by macrophages by expression of the protein in insect cells, preferably using a baculovirus expression system.

Pharmaceutical compositions comprising baculovirus-expressed proteins as a component which are designed for delivery to macrophages are also provided by the present invention.

The therapeutic activity of proteins which may be used to treat lysosomal storage disorders is attributed primarily to the lysosomal activity of such proteins in macrophages. Therefore these proteins particularly benefit from the targeting achieved by the present invention. Such proteins include Cathepsin A/Protective Protein (PPCA), lysosomal neuraminidase, β-galactosidase and all other proteins identified in Table 1.

The present invention also provides a method for causing a cell to import a protein produced in insect cells through expression of a mannose receptor on the membrane of the cell. This method may be achieved, for example, by engineering the cell to express a mannose receptor or by providing mannose receptor protein to the cell.

The present invention further provides a targeting system whereby a desired protein is targeted for delivery into a desired cell by expressing the protein in a baculovirus expression system and causing the cell to express a mannose receptor on its membrane.

DETAILED DESCRIPTION OF THE INVENTION

Definitions:

The following terms and phrases used in this application are intended to have the following meanings:

"Baculovirus expression system" means a system for producing a desired protein in an insect cell using a recombinant baculovirus vector designed to express the protein at high levels. The steps involved in using a baculovirus expression system are (a) engineering a baculovirus vector to express a desired protein at high levels, (b) introduction of the engineered baculovirus vector into insect cells, (c) culturing the insect cells containing the engineered baculovirus vector in a suitable growth medium such that the desired protein is expressed at high levels, and (d) recovering the protein from the culture medium. Preferably the protein is recovered from the culture medium via purification on a ConA column using methyl-α-D-Manno-Pyrano-side (Sigma # M-6882) in the elution buffer. Typically, engineering a baculovirus vector involves the construction and isolation of recombinant Baculoviruses in which the coding sequence for a chosen gene is inserted behind the promoter for a nonessential viral gene, polyhedrin or p10 (fibrous body protein Ac-p10 or AcOrf-137; protein ID No. NP_054167.1, nucleotides 118839–119123 of the *Autographica californica* nucleopolyhedrovirus genome ID No. NC 001623).

Baculovirus expression systems are well know in the art and have been described, for example, in "Baculovirus Expression Vectors: A Laboratory Manual" by David R. O'Reilly, Lois Miller, Verne Luckow, pub. by Oxford Univ. Press (1994), "The Baculovirus Expression System: A Laboratory Guide" by Linda A. King, R. D. Possee, pub. by Chapman & Hall (1992); U.S. Pat. Nos. 6,225,060; 6,183,987; 6,090,584; 5,658,567; 5,877,019; 5,869,336; 5,861,279; 5,726,024; 5,571,709; 5,516,657; 5,472,858; 5,278,050; 5,244,805; 5,229,293; 5,194,376; 5,179,023; 5,110,729; and the Bac-to-Bac Baculovirus Expression System; Invitrogen Cat. No. 10359016.

"Insect cell" means a cell or cell culture derived from an insect species. Of particular interest with respect to the present invention are insect cells derived from the species *Spodoptera frugiperda* and *Trichoplusia ni.*

"Mannose receptor" means a protein receptor that recognizes the patterns of carbohydrates that decorate the surfaces and cell walls of infectious agents and certain proteins and mediates the import of proteins and cells that have the recognized pattern of carbohydrates. Mannose receptors naturally occur on the membranes of certain cells including, but not necessarily limited to:

(a) macrophages (see, e.g., Roulieux-Bonnin, F. et al., *Biochem. Biophys. Res. Comm.* 217: 106–112 (1995)), immature dendritic cells (see Reis, E. et al., *J. Exp. Med.* 178: 509–519 (1993) and Sallusto, F. et al., *J. Exp. Med.* 182: 389–400 (1995)), (b) certain endotheliel cells (see Magnusson, S. et al., *Biochem. J.* 291: 749–755 (1993) and Bijsterbosch, M. K. et al., *Eur. J. Biochem.* 237: 344–349 (1996)), (c) tracheal smooth muscle cells (see Lew, D. B. et al., *J. Clin. Invest.* 88: 1969–1975 (1991) and Lew, D. B. et al., *J. Clin. Invest.* 94: 1855–1863 (1994)), (d) retinal pigmental epithelium (see Lutz, D. A. et al., *Exp. Eye Res.* 61: 487–493 (1995) and Shepard, V. L. et al., *Invest. Ophthamol. Vis. Sci.* 32: 1779–1784 (1991)), (e) kidney mesangial cells (see Liu, Z. H. et al., *Am. J. Physiol.* 270: C1595–1601 (1996)), and (f) Kaposis sarcoma cells (see Uccini, S. et al., *Am. J. Pathol.* 150: 929–938 (1997).

Mannose receptors mediate endocytosis and phagocytosis. The mannose receptor is the prototype of a new family of multilectin receptor proteins and provides a link between innate and adaptive immunity. See also Stahl, D. et al., "The mannose receptor is a pattern recognition receptor involved in host defense", *Curr. Biol.* 10: 50–55 (1998); Taylor, M. E., "Structure and function of the macrophage mannose receptor" in *Results and problems in cell differentiation, Vol.* 33; Crocker, P. R. (Ed); Springer-Verlag (2001); and Stehle, S. E. et al., "A soluble mannose receptor immunoadhesin enhances phagocytosis of Pneumocystis carinii by human polymorphonuclear leukocytes in vitro", *Scand. J. Immunol.* 52: 131–137 (2000).

"Pharmaceutically acceptable carrier" means any and all solvents, dispersion media, coatings, antibacterial and antifungal agents, isotonic and absorption delaying agents and the like. The use of such media and agents with active ingredients to create pharmaceutical compositions is well known in the art. See, e.g. "Remington's Pharmaceutical Sciences" by E. W. Martin. Except insofar as any conventional media or agent is incompatible with the active ingredient used, its use in pharmaceutical compositions of the invention is contemplated.

"Protein-conjugate complex" is used herein to refer generally to a composition comprising an agent attached to a protein. In the context of the present invention, a protein conjugate complex comprises an agent which is attached to a protein produced in an insect cell for the purpose of targeting the agent to cells which express mannose receptors on their membranes, particularly including macrophages.

"Subject" for purposes of this invention means an animal, particularly including a human.

"Therapeutically effective amount" or "pharmaceutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host, e.g., the reduction of lysosomal storage or shrinkage of a tumor.

Description:

The inventors have discovered an unexpected advantage of using insect cells to produce proteins. As taught herein, proteins produced via expression in insect cells have a glycosylation pattern which renders them susceptible to selective uptake by cells which express mannose receptors on their membranes, such as macrophages. Accordingly, the present invention provides a simple method for producing a protein of interest in a form which will be selectively taken up by macrophages or other cells having mannose receptors on their membranes.

For purposes of the present invention, the method used to express a protein of interest in an insect cell is not critical; any method which results in expression of the protein of interest in an insect cell may be used, as long as such method does not disturb glycosylation of the protein by the insect cell. For example, an insect cell may be stably transformed with a gene encoding the protein of interest and propagated under conditions which cause the gene to be expressed. See, e.g., Express Insect(tm) Vector Set Non-Viral Insect Expression System, Invitrogen Cat. No. 12249017. The Express INsect Non-Viral Insect Expression System is designed for continuous expression of heterologous proteins in Lepidopteran insect cells. It is a plasmid-based, non-lytic system for stable expression. The system uses Gateway Cloning Technology to create the Expression Clone easily. Alternatively, traditional restriction endonuclease cloning can be used. More preferably, the protein of interest may be produced in an insect cell using a Baculovirus expression system. While any insect cell that is useful for foreign protein expression may be used, *Spodoptera frugiperda* or *Tricoplusia ni* cells are preferred, particularly the *Spodoptera frugiperda* cell lines designated Sf9 and Sf21.

Once a protein of interest is expressed in an insect cell, it may be purified for use in accordance with the present invention by conventional methods which preserve the glycosylation pattern of the expressed protein or enhance the occurrence of exposed mannose residues. A protein of interest produced from stably transformed insect cells may be purified using standard techniques such as ammonium sulfate precipitation and column chromatography (cation and anion exchange (resource S and Q columns); gel filtration (Sephacryl 200 high resolution) Amersham-Pharmacia Biotech). See, e.g. Calhoun et al., *Proc. Natl. Acad. Sci. USA* 82: 7364–7368 (1985). A protein of interest produced using a baculovirus expression system may be purified using these same techniques (see Examples 2 and 3). Preferably, the protein is purified on a Concanavalin A-Sepharose column ("Con-A column"; Cat. No. 17-0440-03, Amersham-Pharmacia Biotech). Rather than eluting the protein from the Con-A column with a standard elution buffer containing methyl-α-D-gluco-pyranoside, proteins produced by insect cells are eluted more efficiently with an elution buffer containing methyl-α-D-manno-pyranoside due to their glycosylation pattern. The use of a mannoside-containing buffer to elute proteins produced by insect cells from a Con-A column represents another aspect of the present invention.

As taught by the present invention, proteins produced via expression in insect cells exhibit a unique glycosylation pattern that includes exposed mannose residues. As a result, proteins expressed in insect cells are recognized by mannose receptors and taken up by cells which express mannose receptors on their membranes. This particularly includes macrophages, immature dendritic cells, certain endothelial cells, tracheal smooth muscle cells, retinal pigmental epithelium, kidney mesangial cells, Kaposis sarcoma cells, and cells engineered to express mannose receptors on their membranes.

In one aspect, the present invention provides a method for targeting a protein to macrophages by producing it in an insect cell. Proteins produced via insect cell expression have exposed mannose residues and are selectively imported into macrophages, which naturally express mannose receptors.

The present invention finds particular use in enzyme replacement therapy (ERT) for lysosomal storage disorders (LSDs). Macrophages and the reticulo endothelial system represent a prominent site of pathology for many LSDs. The present invention provides a way to target these sites of pathology via ERT using proteins produced in insect cells.

The effectiveness of treating LSDs by targeting macrophages and the reticulo endothelial system is supported by the study of an LSD in a transgenic mouse model. In this study, transgenic mice suffering from a deficiency in Protective protein/cathepsin A (PPCA) were transplanted with bone marrow from transgenic mice overexpressing PPCA exclusively in tissue macrophages and microglia. The treatment, which only recovered PPCA in macrophages and microglia, completely corrected systemic pathology in the transgenic mice. Hahn et al., *Proc. Natl. Acad. Sci.* 95: 14880–14885 (1998).

LSDs may be treated according to the present invention by producing the appropriate protein(s) in an insect cell culture and administering a therapeutically effective amount to the subject who is suffering from a deficiency of this protein. Thus, for example, a subject suffering from Galactosialidosis would be treated with protective protein/cathepsin A (PPCA), neuraminidase, and/or β-Galactosidase produced in insect cells, a subject suffering from sialidosis would be treated with α-neuraminidase produced in insect cells, and a subject suffering from GM1-gangliosidosis would be treated with β-galactosidase produced in insect cells. With respect to Galactosialidosis, treatment with both PPCA and neuraminidase is preferred over treatment with PPCA alone based on experimental results showing that neuraminidase activity in PPCA deficient macrophages treated with a mix of baculovirus-expressed neuraminidase and PPCA was ten-fold higher than in PPCA deficient macrophages treated with PPCA alone.

Pharmaceutical compositions comprising proteins produced via insect cell expression are also contemplated by the present invention. Such compositions will comprise a protein or an active fragment or derivative thereof which is therapeutically active in a cell which expresses mannose receptors, particularly a macrophage, in a therapeutically effective amount combined with a pharmaceutically acceptable carrier. The components of the pharmaceutical composition other than the therapeutically active protein will vary depending upon the properties of the therapeutically active protein, the route of administration, the desired form of the composition (e.g. tablet, capsule, pill, injectable, etc.), and other variables recognized by those of skill in the art.

Accordingly, the subject invention contemplates treating LSDs resulting from an enzyme deficiency by administering a pharmaceutical composition containing a pharmaceutically effective amount of the missing or deficient enzyme or an active fragment or derivative thereof. By active fragments is meant any part of the enzyme which is derived from the intact whole enzyme and still retains biological activity. Likewise, derivatives refer to enzymes which have been chemically modified or genetically engineered to effect minor changes, for example amino acid substitutions, which maintain biological activity.

The active ingredients of the pharmaceutical compositions comprising recombinant enzyme are contemplated to exhibit excellent and effective therapeutic activity in replacing the enzymatic deficiency found in the associated LSD. Thus, the active ingredients of the therapeutic compositions including recombinant .enzyme exhibit enzymatic activity when administered in therapeutic amounts from about 0.1 ug to about 2000 ug per kg of body weight per day. The dosage regimen may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, intravenous, intranasal, intradermal, subcutaneous, or suppository routes. Depending on the route of administration, the active ingredients of a recombinant pharmaceutical composition may be required to be coated in a material to protect said ingredients from the action of enzymes, acids or other natural conditions.

The active proteins may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Coatings for enzyme preparations are useful to reduce degradation of the enzyme when administered as a therapeutic agent. Coatings also reduce the immunogenicity of the enzyme to help prevent undesirable side effects of administering such a therapeutic agent. A particularly useful coating to provide these characteristics is polyethylene glycol.

Sterile injectable solutions are prepared by incorporating the active enzymes in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When recombinant protein is suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparation should contain at least 1% of active enzyme. The percentage of the compositions and preparations may, of course, be varied and may conveniently be between about 5 to about 80% of the weight of the unit. The amount of active compound in such therapeutically useful compositions is such that a suitable dosage is obtained. Preferred compositions or preparations according to the present invention are prepared so that an oral unit dosage form contains between about 10 ug and 1000 ug of active enzyme.

The tablets, troches, pills, capsules and the like may also contain the following: A binder such as gum agragacanth, acacia, corn starch or gelatin; excipients such as dicalcium phosphate; a disintegrating agent such as corn starch, potato starch, alginic acid and the like; a lubricant such as magnesium stearate; a sweetening agent such as sucrose, lactose or saccharin or a flavoring agent such as peppermint, oil of wintergreen, or cherry flavoring. When the dosage form is a capsule, it may contain, in addition to materials of the above type, a liquid carrier. Various other materials may be present as coatings or to otherwise modify the physical form of the unit dosage. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

It is especially advantageous to formulate parenteral compositions in dosage unit form for ease of administration and uniformity of dosage. Unit dosage form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health impaired as herein disclosed in detail.

The principal active ingredient is compounded for convenient and effective administration in pharmaceutically effective amounts with a suitable pharmaceutically acceptable carrier in dosage unit form as hereinbefore disclosed. A unit dosage form can, for example, contain the principal active compound in amounts ranging from 10 ug to about 1000 ug. Expressed in proportions, the active enzyme is generally present in from about 10 ug to about 1000 ug/ml of carrier. In the case of compositions containing supplementary active ingredients, the dosages are determined by reference to the usual dose and manner of administration of the said ingredients.

In another aspect of the invention, an agent is targeted to macrophages or other cells having mannose receptors by conjugating the agent to a protein produced via expression in insect cells. Such an agent may comprise any substance which can be conjugated with a protein produced in an insect cell, including but not limited to a small molecule, a peptide, and a polypeptide, particularly an antibody.

In yet another aspect of the invention, a cell is rendered receptive to uptake of proteins produced via expression in insect cells by causing the cell to express mannose receptors on its membrane. One may cause the cell to express mannose receptors, for example, by engineering the cell to contain a gene capable of expressing a mannose receptor. Alternatively, the cell may be contacted with mannose receptor protein under conditions which induce incorporation of the mannose receptor protein into the membrane of the cell.

The present invention may be better understood by reference to the following non-limiting examples. These examples are presented in order to more fully illustrate the invention through the description of particular embodiments. These examples should in no way be construed as limiting the scope of the invention.

EXAMPLES

Example 1

Correction of Lysosomal PPCA and Neuraminidase in Mouse Deficient Macrophages after Uptake of Recombinant Baculovirus-expressed Proteins Galactosialidosis (GS) is a lysosomal storage disorder caused by combined deficiency of protective protein/cathepsin A (PPCA), β-galactosidase, and neuraminidase (neur). Patients develop a multi-systemic disease mostly accompanied by severe neurological deficit and early death. Their clinical symptoms are similar to those of sialidosis patients and have been mainly attributed to the secondary deficiency of neur. The dependence of neur to PPCA for intracellular targeting and activation underscores the need for therapeutic modalities that would supply the patients with both enzymes. Recombinant PPCA precursor is secreted efficiently from normal and over-expressing mammalian cells, and can be taken-up by deficient fibroblasts and other cells via the M6P receptor, correcting the enzyme deficiency. In contrast, neur, although secreted, lacks a functional M6P recognition marker and is internalized poorly by mammalian cells. With the intent to investigate the potential of ERT for the treatment of GS recombinant baculovirus-expressed proteins (BV-neur and BV-PPCA) were used as the source of the corrective enzymes.

The recombinant baculovirus expressed proteins are biologically functional and can be produced in large quantities at low cost. BV-neur and BV-PPCA were tested in uptake experiments on cultured bone marrow (BM) macrophages. Both BV-PPCA and BV-neur, either alone or mixed, were efficiently taken up by PPCA-deficient mouse macrophages, and capable of restoring cathepsin A and neuraminidase activities. Maximum correction of neuraminidase activity (>10 fold control values) was established with a mixture of PPCA and neur. Uptake was blocked by the addition of yeast mannan, indicating that the proteins were taken up via the mannose receptor present on the membranes of macrophages.

Baculovirus-expressed and purified neuraminidase and PPCA were also injected into PPCA deficient mice. The mice were injected 3 times a week over a two-week period with a constant dose of 100 μg of neuraminidase and 50 μg of PPCA dissolved in 200 μl of phosphate buffered saline (PBS). Following treatment, the mice were sacrificed and tissues were analyzed by biochemical and imunohistochemical assays. The cathepsin A and neuraminidase activities were were significantly increased in several of the systemic organs. Immuno and histological staining of the liver showed the presence of the therapeutic protein (PPCA) in macrophages and resolution of lysosomal storage.

These results set the basis for ERT trials in PPCA and neur deficient mouse models, using BV-derived recombinant proteins. The use of BV-produced proteins is also contemplated to be applicable to other lysosomal disorders.

Example 2

Methods for the Large Scale Production of PPCA and Neuraminidase in Insect Cells and Purification of these Proteins from the Culture Medium.

Sf9 cells are propagated in SFX medium (Hyclone) in disposable 2L-Erlenmeyers (Coming) using an orbital shaker-incubator at 27° C. and 135 r.p.m. On the day of the virus infection the cells are diluted in fresh medium to a density of $1 \times 10^6$ cells/ml (6 liters total volume).

Either the PPCA or neuraminidase recombinant baculovirus is added to the flasks at a M.O.I. of 1 (1 virus particle per cell) followed by incubation in the shaker-incubator. Three days after the initiation of infection the medium is separated from the cells by centrifugation and filtered through a 0.2 μm filter. After addition of 600 ml Phosphate Buffered Saline solution (10× PBS) the medium is pumped over two columns, each containing 15 ml Con A.

All subsequent purification steps are performed at either pH 8 for neuraminidase or pH 6.5 for PPCA. pH control is crucial because PPCA is unstable above pH 7 and neuraminidase will be lost due to precipitation below pH 7).

The Con A columns are washed with (i) 150 ml of 20 mM Phosphate/0.5M NaCl, (ii) 150 ml of 20 mM Phosphate/1M NaCl, followed by (iii) a pre-elution step with 100 ml of 20 mM Phosphate/0.5 NaCl and 25 mM Methyl-α-D-Mannopyranoside (eluate). Neuraminidase and PPCA do not elute from the Con A columns at this low concentration of eluate. However, this step allows for the near complete removal of the viral protein Ecdysteroid UDP-Glucosyltransferase (EGT, Genbank: P18569). This is the major contaminant protein secreted by the infected Sf9 cells in the insect cell medium. This pre-elution step may also be applicable in the Con A-purification of other baculovirus/insect cell produced glycosylated proteins.

PPCA and neuraminidase are eluted from the Con A columns at 37° C. with 150 ml of 20 mM Phosphate/0.5M NaCl and 1M Methyl α-D-Manno-pyranoside (high concentration eluate). Subsequently, the proteins may be further purified by gel filtration chromatograpy on Sephacryl 200-HR columns (Amersham-Pharmacia) and ion exchange chromatography (Amersham-Pharmacia: Resource-s for PPCA, and Resource-q for neuraminidase). The final purity of both PPCA and neuraminidase is >95% with yields ranging between 5–15 mg protein.

Various publications, patent applications and patents are cited herein, the disclosures of which are incorporated by reference in their entireties.

We claim:

1. A pharmaceutical composition comprising a protein useful for treating a lysosomal storage disorder other than Fabry disease that is selectively imported into macrophages when administered to a subject and a pharmaceutically acceptable carrier, wherein said protein is produced in an insect cell culture and is selected from the group consisting of acid α-1,4 glucosidase, acid α-1,6 glucosidase, β-galactosidase, β-hexosaminidase A, $GM_2$ Activator Protein, β-hexosaminidase A, β-hexosaminidase B, glucocerebrosidase, β-glucosidase, galactosylcerebrosidase, acid sphingomyelinase, acid ceramidase, acid lipase, α-L-iduronidase, iduronate sulfatase, α-N-acetylglucosaminidase, acetyl-CoA-glucosaminide acetyltransferase, N-acetylglucosamine-6-sulfatase, galactosamine-6-sulfatase, arvlsuylfatase B, β-glucuronidase, arylsulfatase A, arylsulfatase C, α-Neuraminidase, UDP GlcNAc:lysosomal-enzyme N-acetylglucosamine-1-phosphotransferase, neuraminidase, α-mannosidase, β-mannosidase, α-L-fucosidase, N-aspartyl-β-glucosaminidase, protective proteinlcathepsin A (PPCA), α-N-acetyl-galactosaminidase, cystine transport protein, sialic acid transport protein, palmitoyl-protein thioesterase, and Saposins A–D.

2. The composition of claim 1 wherein said lysosomal storage disorder is Galactosialidosis.

3. The composition of claim 1 wherein said protein is protective protein/cathepsin A (PPCA).

4. The composition of claim 1 wherein said insect cell culture comprises cells derived from the species selected from the group consisting of *Spodoptera frugiperda* and *Tricoplusia ni*.

5. The composition of claim 4 wherein said cells are *Spodoptera frugiperda* Sf9 cells.

6. The composition of claim 1 wherein said protein is produced in the cell culture using a baculovirus expression system.

7. The composition of claim 1 wherein said lysosomal storage disorder and associated protein useful for treating said lysosomal storage disorder are selected from the group consisting of Pompe Disease and acid α-1,4 glucosidase, Pompe Disease and acid α-1,6 glucosidase, GM1 gangliosidosis and β-galactosidase, Tay-Sachs disease and β-hexosaminidase A, GM2 gangliosialidosis: AB Variant and $GM_2$ Activator Protein, Sandhoff Disease and β-hexosaminidase A, Sandhoff Disease and β-hexosaminidase B, Gaucher Disease and glucocerebrosidase, Gaucher Disease and β-glucodase, Krabbe Disease and galactosylcerebrosidase, Niemann-Pick Type A and acid sphingomyelinase, Niemann-Pick Type B and acid sphingomyelinase, Farber Disease and acid ceramidase, Wolman Disease and acid lipase, Cholesterol Ester Storage Disease and acid lipase, Hurler Syndrome and α-L-iduronidase, Schie Syndrome and α-L-iduronidase, Hurler-Schie and α-L-iduronidase, Hunter Syndrome and iduronate 2-sulfate, Sanfilippo A and α-N-acetylglucosaminidase, Sanfilippo B and α-N-acetylglucosaminidase, Sanfilippo C and acetyl-CoA-glucosaminide acetyltransferase, Sanfilippo D and N-acetylglucosamine-6-sulfatase, Morquito A and N-acetylglucosamine-6-sulfate sulfatse, Morquito B and β-galactosidase, Maroteaux-Lamy and arylsuylfatase B, Sly Syndrome and β-glucuronidase, Metachromatic Leukodystrophy and arylsulfatase A, Multiple Sufatase Deficiency and arylsulfatase A, Multiple Sulfatase Deficiency and arylsulfatase B, Multiple Sulfatase Deficiency and arylsulfatase C, Sialidosis and α-Neuraminidase, I-Cell Disease and UDP GicNAc: lysosomal-enzyme N-acetylglucosamine-1-phosphotransferase, Pseudo-Hurler Polydistrophy and UDP GicNAc: lysosomal-enzyme N-acetylglucosamine-1-phosphotransferase, Mucolipidosis IV and mucolipin-1, α-Mannosidosis and α-mannosidase, β-Mannosidosis and β-mannosidase, Fucosidosis and α-L-fucosidase, Aspartylglucosaminuria and N-aspartyl-β-glucosaminidase, Galactosialidosis and protective protein/cathepsin A, Galactosialidosis and neuraminidase, Galactosialidosis and β-galactosidase, Schindler Disease and α-N-acetyl-galactosaminidase, Cystinosis and cystine transport protein, Salla Disease and sialin, Infantile Sialie Acid Storage Disorder and sialin, Infantile Neuronal Ceroid Lipofuscinosis and palmitoyl-protein thioesterase, Prosaposin and Saposin A, Prosaposin and Saposin B, Prosaposin and Saposin C, and Prosaposin and Saposin D.

8. The composition of claim 7 wherein said lysosomal storage disorder is Sialidosis and said protein useful for treating said lysosomal storage disorder is a β-Neuraminidase.

* * * * *